(12) United States Patent
Graves

(10) Patent No.: US 9,955,683 B2
(45) Date of Patent: May 1, 2018

(54) INSECTICIDAL APPARATUS AND METHODS

(71) Applicant: AmeriAg, LLC, Burlington, NC (US)

(72) Inventor: Travis Graves, Burlington, NC (US)

(73) Assignee: AMERIAG, Burlington, NC (US)

( * ) Notice: Subject to any disclaimer, the term of this patent is extended or adjusted under 35 U.S.C. 154(b) by 732 days.

(21) Appl. No.: 14/019,285

(22) Filed: Sep. 5, 2013

(65) Prior Publication Data

US 2014/0161857 A1    Jun. 12, 2014

Related U.S. Application Data

(60) Provisional application No. 61/787,144, filed on Mar. 15, 2013, provisional application No. 61/697,024, filed on Sep. 5, 2012.

(51) Int. Cl.
*A01N 25/10* (2006.01)
*A01N 25/34* (2006.01)

(52) U.S. Cl.
CPC ............. *A01N 25/10* (2013.01); *A01N 25/34* (2013.01)

(58) Field of Classification Search
CPC .................................. A01N 25/10; A01N 25/34
USPC ................................................... 424/409, 416
See application file for complete search history.

(56) References Cited

U.S. PATENT DOCUMENTS

| | | | |
|---|---|---|---|
| 4,265,876 A | 5/1981 | Feakins | |
| 4,279,085 A * | 7/1981 | Arnold | E02F 3/40 172/699 |
| 4,428,327 A | 1/1984 | Steckel | |
| 4,543,247 A | 9/1985 | Von Bittera et al. | |
| 4,544,547 A | 10/1985 | Von Bittera et al. | |
| 4,579,085 A * | 4/1986 | McGuire | A01K 13/003 119/655 |
| 4,666,767 A | 5/1987 | Von Kohorn et al. | |
| 4,803,956 A | 2/1989 | Corrigan et al. | |
| 4,875,837 A | 10/1989 | Usami et al. | |
| 5,394,832 A * | 3/1995 | Briley | A01K 5/01 119/51.11 |
| 5,472,955 A | 12/1995 | Kellerby | |
| 8,545,762 B2 * | 10/2013 | Lin | G01N 21/78 422/86 |
| 2003/0152483 A1 * | 8/2003 | Munagavalasa | G01N 31/229 422/400 |
| 2004/0202690 A1 | 10/2004 | Arther et al. | |
| 2008/0115737 A1 | 5/2008 | Arther et al. | |
| 2009/0004236 A1 | 1/2009 | Kellerby | |
| 2012/0017838 A1 | 1/2012 | Graves | |

OTHER PUBLICATIONS

"Livestock identification and pest control systems", Y-Tex Corporation, Jun. 25, 2012, pp. 1, ytex.com, United States.
"Dust Bag Kits", Agrilabs, Jun. 28, 2012, pp. 1, jefferslivestock.com, United States.
"Pest Doom Oiler", Enasco, Jun. 28, 2012, pp. 1, enasco.com, United States.
"Cow Life-Cattle Rub", P.H. White Co., Jul. 9, 2012, pp. 1-28, phwhite.com, United States.
Russ Gentry, "From the Farm: Jun. 2001," May 16, 2012, pp. 1, The Samuel Roberts Noble Foundation, Inc.
"Allflex Sales Territories", Allflex USA, Inc., Jun. 25, 2012, pp. 1-2, allflexusa.com, United States.
Stephen J. Toth, Jr. and Thomas A. Melton, "North Carolina Pest News—vol. 19, No. 1, Apr. 16, 2004", pp. 1-3, Jun. 25, 2012, NC State College of Agriculture and Life Sciences, United States.
"Methods of Treatment", Merck Veterinary Manual, Jun. 11, 2012, pp. 1-2, merchvetmanual.com, United States.
"Haematobia irritans", Wikipedia, Jun. 11, 2012, pp. 1-4, wikipedia.org.
"Fly Control on Cattle is Critical", Drovers CattleNetwork, Jun. 11, 2012, pp. 1-2, cattlenetwork.com, United States.
"Pyrethoid", Wikipedia, Jun. 11, 2012, pp. 1-4, wikipedia.org.
"Factsheet: The Use of Insecticide-Impregnated Cattle Ear Tags on the Halters of Horses", Ontario Ministry of Agriculture, Food and Rural Affairs, Aug. 2006, pp. 1-4, Canada.
Lee Townsend, "Insecticide-Impregnated Ear Tags", University of Kentucky College of Agriculture, pp. 1-2, United States.
"Ectoparasiticides Used in Large Animals: Overview", Merck Veterinary Manual, pp. 1-10, merckbooks.com.

* cited by examiner

*Primary Examiner* — Johann R Richter
*Assistant Examiner* — Courtney A Brown
(74) *Attorney, Agent, or Firm* — Jenkins, Wilson, Taylor & Hunt, P.A.

(57) ABSTRACT

Insecticidal apparatus and methods are provided for controlling or managing insect pests and ectoparasites. An apparatus for administering an insecticidal compound to a subject can include a material for absorbing an insecticidal compound and an insecticidal compound. An insecticidal apparatus can include an attachment element for attaching the apparatus to a desired location. Insect pests or ectoparasites can be controlled or managed on subjects or animals coming into contact with or in proximity to an insecticidal apparatus as disclosed herein.

3 Claims, 7 Drawing Sheets

INSECTICIDAL APPARATUS AND METHODS

CROSS-REFERENCE TO RELATED APPLICATIONS

This application claims the benefit of and priority to U.S. Provisional Application No. 61/697,024, filed Sep. 5, 2012, and U.S. Provisional Application No. 61/787,144, filed Mar. 15, 2013, the entire disclosure of each of which is herein incorporated by reference.

TECHNICAL FIELD

This presently disclosed subject matter relates to methods and devices for ectoparasite control. More specifically, the presently disclosed subject matter is directed to an ectoparasiticide device or material for use in controlling ectoparasites, pests and insects on and around livestock animals, domesticated animals, human subjects, homes and businesses. The disclosed ectoparasiticide devices and materials are designed to be durable, versatile, and in some embodiments reusable, for numerous applications where ectoparasite control is needed.

BACKGROUND

In the livestock industry, fly and pest control management is important for the welfare and performance of livestock animals. Flies and other parasites, also referred to as ectoparasites, can negatively impact livestock health and well-being by causing health problems such as compromised immunity and disease. Animal performance, such as milk production and/or weight gain, can also be negatively impacted by flies, pests, parasites and ectoparasites. Existing methods and devices used to manage pests and ectoparasites in the livestock industry have limited effectiveness and numerous drawbacks.

Pest control management is also important for human comfort and safety. Flies, mosquitoes, ticks and other pests and ectoparasites can be problematic for humans both indoors and outdoors. Likewise, pets and other domestic animals can also be affected by pests and ectoparasites.

Insecticides suitable for managing pests and ectoparasites, also referred to as ectoparasiticides, often come in liquid and powder form. Liquid forms can be applied directly onto an animal or subject. Other liquid insecticides can be applied to a transfer medium that allows an animal or subject to self-apply the insecticide. For example, in the livestock industry, rubs, wicks and devices placed near feeding areas, e.g. "bullets", allow an animal to self-apply insecticide to themselves as the animal comes into contact with the applicator, e.g. by walking past or rubbing up against the applicator. Timed or automatic devices can also spray the animal directly with the insecticide, such as a spray attachment to a mineral feeder. However, each of the currently available devices and applicators for administering an insecticide to treat and/or manage pests and/or ectoparasites has significant drawbacks that limit their effectiveness.

What is needed is an improved methods and devices for delivering and administering insecticides and/or ectoparasiticides directly to and/or in the vicinity of livestock animals, domesticated animals, and/or human subjects.

SUMMARY

It is an object of the presently disclosed subject matter is directed to methods and devices for ectoparasite control. The presently disclosed subject matter is directed in some embodiments to an ectoparasitic apparatus or material for use in controlling ectoparasites and pests in livestock and domesticated animals as well as controlling ectoparasites and other insect pests around people, homes and businesses.

An object of the presently disclosed subject matter having been stated hereinabove, and which is achieved in whole or in part by the presently disclosed subject matter, this and other objects will become evident as the description proceeds when taken in connection with the accompanying drawings as best described hereinbelow.

BRIEF DESCRIPTION OF THE DRAWINGS

The features and advantages of the present subject matter will be more readily understood from the following detailed description which should be read in conjunction with the accompanying drawings that are given merely by way of explanatory and non-limiting example, and in which.

DETAILED DESCRIPTION

Figure 1:
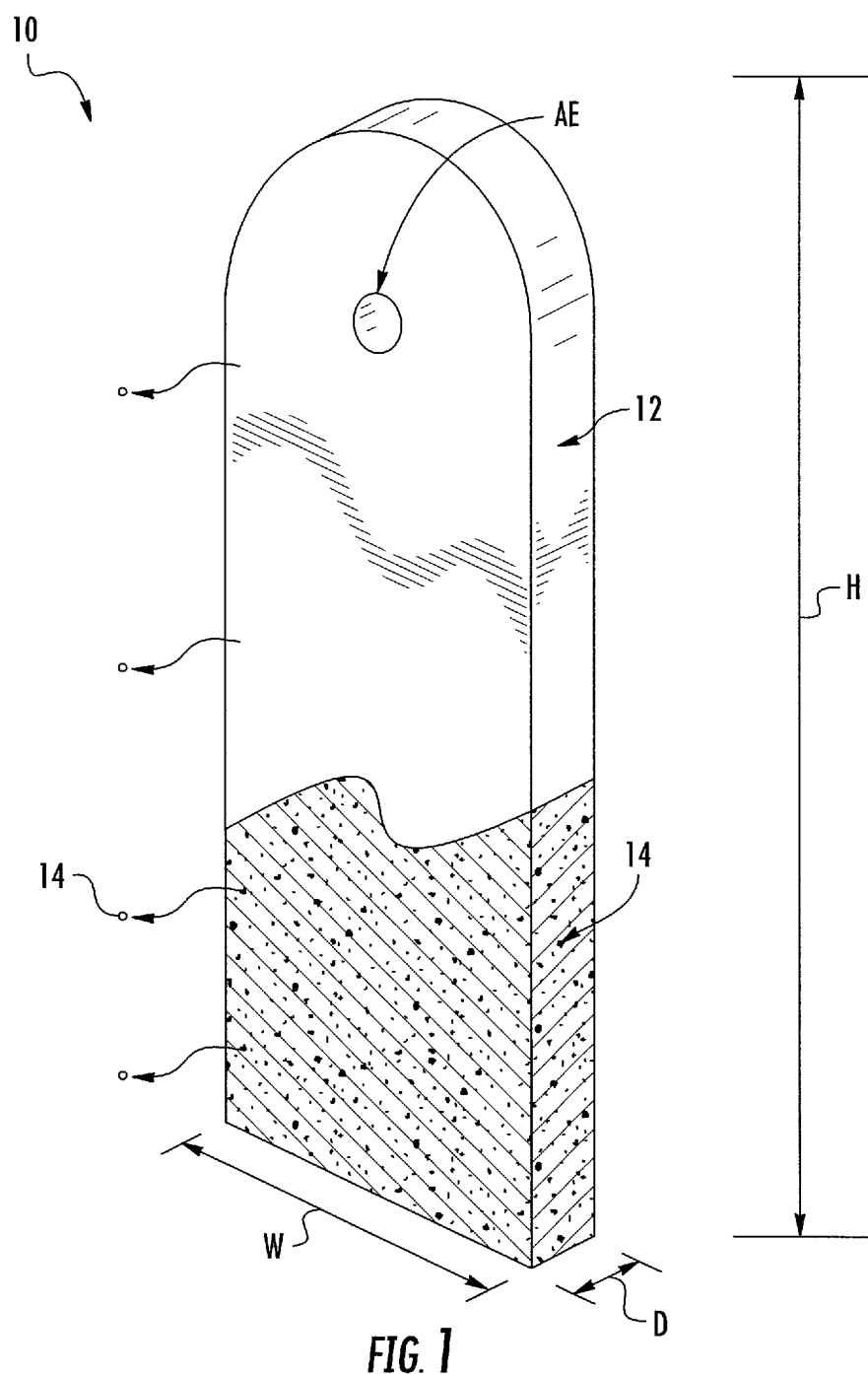
FIG. 1 is a perspective view, with partial cut-away view, of an elongated strip embodiment of an apparatus in accordance with the subject matter herein.

The subject matter disclosed herein provides methods and devices for insect pest and ectoparasite control in animals and humans. In some aspects, the presently disclosed subject matter is directed to a device or material configured to administer or emit an insecticide or ectoparasiticide for controlling or managing insect pests and/or ectoparasites on and/or around livestock animals, domesticated animals and humans. A device for insect pest and ectoparasite control in accordance with the disclosure herein can be designed to be durable, in some instances reusable, and in some embodiments versatile for numerous applications.

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a fastener" includes a plurality of such fasteners, and so forth.

Unless otherwise indicated, all numbers expressing quantities, units of measure, and so forth used in the specification and claims are to be understood as being modified in all instances by the terms "about", "approximately" and "substantially". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to a weight, volume, distance, measurement, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate with respect to the disclosed subject matter.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the terms "feeder", "livestock feeder" and "mineral feeder" are used interchangeably and refer to an apparatus for providing a feed, feedstuff or supplement to an animal.

The terms "subject" and "animal" as used herein refers to any vertebrate species. The apparatuses and methods disclosed herein are particularly useful in warm-blooded vertebrates. Thus, the presently disclosed subject matter concerns mammals and birds. More particularly provided are apparatuses and methods for controlling insect pests in mammals such as humans, as well as those mammals of importance due to being endangered (such as Siberian tigers), of economic importance (livestock animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. The disclosed apparatuses and methods for controlling insect pests are also applicable to birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, provided is the treatment of livestock, including, but not limited to, domesticated swine, ruminants, horses, poultry, and the like.

FIG. 1 depicts an embodiment of an apparatus 10 configured to administer or emit an insecticide, anti-parasitic compound or ectoparasiticide (hereinafter collectively referred to as "insecticidal compound") for controlling or managing insect pests and/or ectoparasites on and/or around livestock animals, domesticated animals and humans. Apparatus 10 can in some embodiments comprise a material 12 capable of absorbing, or being impregnated with, an insecticidal compound 14. In some embodiments, material 12 can comprise a polyvinylchloride (PVC), polycarbonate, plastic, composite or other material suitable for absorbing an insecticidal compound 14. In some embodiments, material 12 can be in the shape of a strip or elongated member, as depicted in FIG. 1. In some embodiments, material 12 in the shape of a strip can have a depth D, or thickness, of about ¹/₁₆ inch to about 4 inches, a width W of about ½ inch to about 4 inches, and a height H, or length, of about 4 inches to about 36 inches. In some embodiments, material 12 in the shape of a strip can have a depth D, or thickness, of about $\frac{1}{16}^{th}$ inch, about $\frac{1}{8}^{th}$ inch, about ¼ inch, about ½ inch, about ¾ inch, about 1 inch, about 1½ inches, about 2 inches, about 2½ inches, about 3 inches, about 3½ inches, or about 4 inches, a width W of about ½ inch, about ¾ inch, about 1 inch, about 1½ inches, about 2 inches, about 2½ inches, about 3 inches, about 3½ inches, or about 4 inches, and a height H, or length, of about 4 inches, about 5 inches, about 6 inches, about 7 inches, about 8 inches, 9 inches, about 10 inches, about 12 inches, about 18 inches, about 24 inches, about 30 inches, or about 36 inches.

Continuing with FIG. 1, in some aspects insecticidal compound 14 is absorbed into at least a portion of material 12. In some aspects, material 12 of apparatus 10 can be impregnated with insecticidal compound 14 as depicted in the partial cut-away view. In some embodiments, material 12 can comprise a polyvinylchloride (PVC), polycarbonate, plastic, composite or other material capable of absorbing such a compound 14, or capable of being impregnated with compound 14. In some embodiments, insecticidal compound 14 can be impregnated into material 12 by mixing insecticidal compound 14 with material 12 prior to the molding of apparatus 10, following by a baking and/or curing procedure to thereby impregnate material 12 with insecticidal compound 14. In some aspects, apparatus 10 can be made from material 12 by way of molding, such as injection molding, to form the desired shape or configuration.

In some embodiments, insecticidal compound 14 can be administered to an animal or subject that comes into contact with apparatus 10 by virtue of the insecticidal compound 14 transferring to, or rubbing off of apparatus 10 and onto, the animal or subject upon contact between the animal or subject and a surface of apparatus 10. In some aspects, insecticidal compound 14 absorbed into material 12 can migrate to one or more surfaces of apparatus 10, whereby insecticidal compound 14 is administered to an animal or subject that comes into contact with the one or more surfaces of apparatus 10. In some embodiments, insecticidal compound 14 at or near a surface of apparatus 10 can be emitted into the surrounding air by way of dissipation from apparatus 10, as illustrated in FIG. 1. As such, in some embodiment's apparatus 10 can provide for the control or treatment of insect pests and/or ectoparasites in a vicinity of apparatus 10, which can be placed or situated near livestock animals, domesticated animals and humans.

In some aspects, material 12 of apparatus 10 can be recharged or refilled with insecticidal compound 14 by allowing an insecticidal compound to be absorbed into material 10. In some aspects, apparatus 10 can be soaked in, dipped in, or otherwise exposed to an insecticidal compound 14, particularly in liquid form, to thereby recharge or refill an apparatus 10. In some embodiments, apparatus 10 can comprise a color agent, or indicator compound, that fades or changes color as the insecticide compound dissipates or is otherwise used up. Such an indicator compound can indicate to a user that apparatus 10 needs to be changed or recharged in order to maintain a desired insecticidal activity.

In some embodiments, apparatus 10 can comprise an attachment element AE for attaching apparatus 10 to an element to which an animal comes into contact. In some aspects, attachment element AE comprises a hole in material 12, as depicted in FIG. 1, through which a securing element can pass to thereby attach the apparatus to an element to which an animal comes into contact, such as for example a feeder, fence or housing structure. In some aspects, attachment element AE can comprise a slit through material 12, a grommet, a hook molded or formed into material 12, or a loop extending from a surface of material 12. The securing element can comprise a wire, string, hook, snap, button, zip-tie, or any other material suitable for engaging attachment element AE and attaching to an element to which an animal comes into contact.

Figure 2:
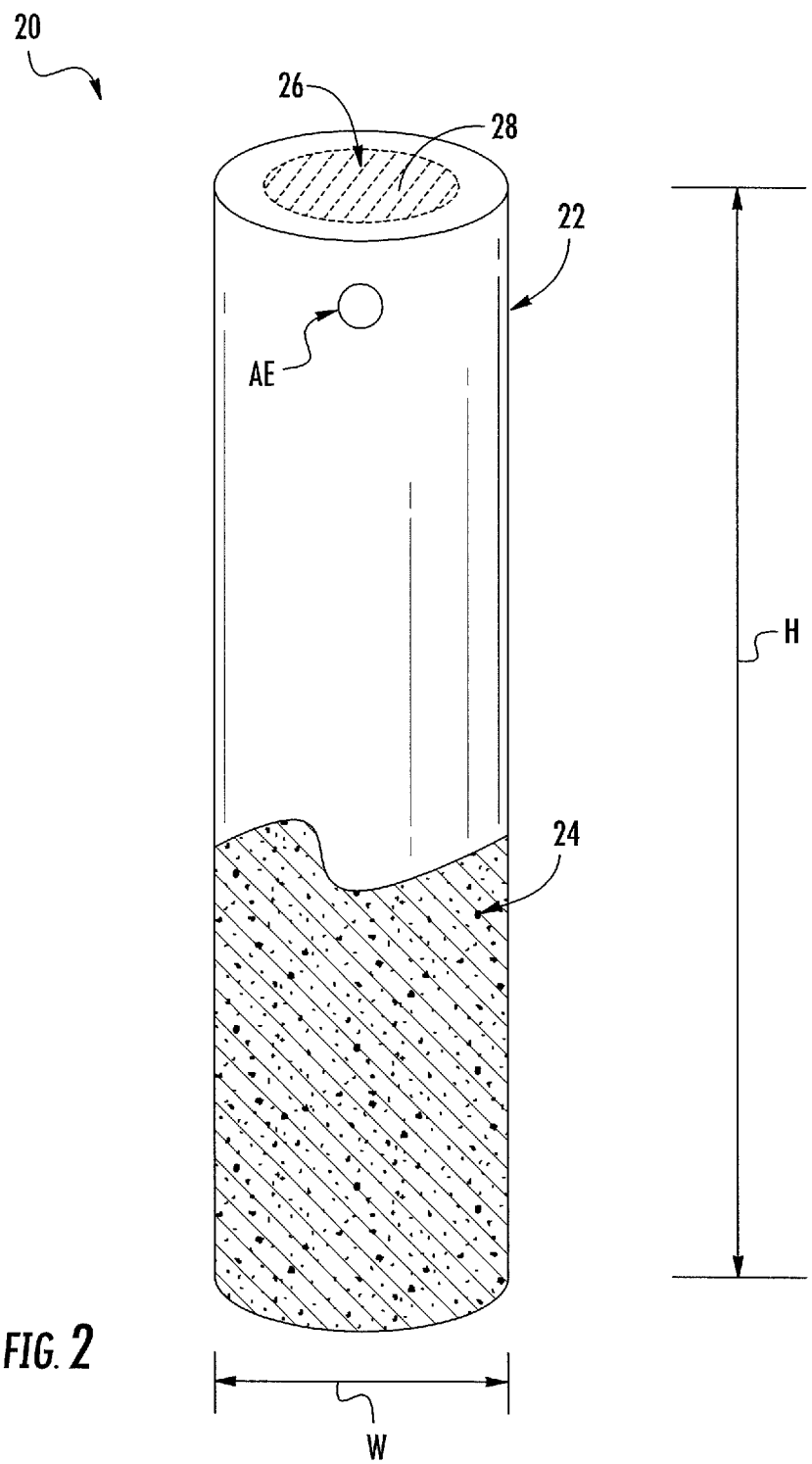
FIG. 2 is a perspective view, with partial cut-away view, of an elongated cylinder embodiment of an apparatus in accordance with the subject matter herein.

FIG. 2 depicts an embodiment of an apparatus 20 configured to administer or emit an insecticidal compound for controlling or managing insect pests and/or ectoparasites on and/or around livestock animals, domesticated animals and humans. Apparatus 20 can in some embodiments comprise a material 22 capable of absorbing, or being impregnated with, an insecticidal compound 24. In some embodiments, material 22 can comprise a polyvinylchloride (PVC), polycarbonate, plastic, composite or other material suitable for absorbing an insecticidal compound 24. In some embodiments, material 22 can be in the shape of a cylinder or elongated cylindrical structure, as depicted in FIG. 2. In some embodiments, material 22 in the shape of an elongated cylinder having a width, or circumference, of about ½ inch to about 4 inches, and a length of about 4 inches to about 36 inches. In some embodiments, material 22 in the shape of a cylinder can have a width W, or circumference, of about % inch, about ¾ inch, about 1 inch, about 1½ inches, about 2 inches, about 2½ inches, about 3 inches, about 3½ inches, or about 4 inches, and a height H, or length, of about 4 inches, about 5 inches, about 6 inches, about 7 inches, about 8 inches, 9 inches, about 10 inches, about 12 inches, about 18 inches, about 24 inches, about 30 inches, or about 36 inches.

Continuing with FIG. 2, in some aspects insecticidal compound 24 is absorbed into at least a portion of material 22. In some aspects, material 22 of apparatus 20 can be impregnated with insecticidal compound 24 as depicted in the partial cut-away view. In some embodiments, material 22 can comprise a polyvinylchloride (PVC), polycarbonate, plastic, composite or other material capable of absorbing such a compound 24, or capable of being impregnated with compound 24. In some embodiments, insecticidal compound 24 can be impregnated into material 22 by mixing insecticidal compound 24 with material 22 prior to the molding of apparatus 20, following by a baking and/or curing procedure to thereby impregnate material 22 with insecticidal compound 24. In some aspects, apparatus 20 can be made from material 22 by way of molding, such as injection molding, to form the desired shape or configuration.

In some embodiments, insecticidal compound 24 can be administered to an animal or subject that comes into contact with apparatus 20 by virtue of the insecticidal compound 24 transferring to, or rubbing off of apparatus 20 and onto, the animal or subject upon contact between the animal or subject and a surface of apparatus 20. In some aspects, insecticidal compound 24 absorbed into material 22 can migrate to one or more surfaces of apparatus 10, whereby insecticidal compound 24 is administered to an animal or subject that comes into contact with the one or more surfaces of apparatus 20. In some embodiments, insecticidal compound 24 at or near a surface of apparatus 20 can be emitted into the surrounding air by way of dissipation from apparatus 20. As such, in some embodiment's apparatus 20 can provide for the control or treatment of insect pests and/or ectoparasites in a vicinity of apparatus 20, which can be placed or situated near livestock animals, domesticated animals and humans.

In some aspects, material 22 of apparatus 20 can be recharged or refilled with insecticidal compound 24 by allowing an insecticidal compound to be absorbed into material 22. In some aspects, apparatus 20 can be soaked in, dipped in, or otherwise exposed to an insecticidal compound 24, particularly in liquid form, to thereby recharge or refill an apparatus 20. In some aspects, material 22 of apparatus 20 can comprise a refillable region 26 where insecticidal compound 24 can be poured, applied, or otherwise administered to thereby recharge apparatus 20 with insecticidal compound 24. In some embodiments, refillable region 26 can comprise a center region of material 22, exposed at one or more surface or ends of apparatus 20 as depicted in FIG. 2. In some aspects, refillable region 26 can comprise an absorbent material 28. In some aspects, insecticidal compound 24 within refillable region 26 can migrate through material 22 to a surface of apparatus 20 such that it is positioned to dissipate into a space surrounding apparatus 20 or be administered to a subject or animal coming into contact with apparatus 20. In some embodiments, apparatus 20 can comprise a color agent, or indicator compound, that fades or changes color as the insecticide compound dissipates or is otherwise used up. Such an indicator compound can indicate to a user that apparatus 20 needs to be changed or recharged in order to maintain a desired insecticidal activity.

In some embodiments, apparatus 20 can comprise an attachment element AE for attaching apparatus 20 to an element to which an animal comes into contact. In some aspects, attachment element AE comprises a hole in material 22, as depicted in FIG. 2, through which a securing element can pass to thereby attach the apparatus to an element to which an animal comes into contact, such as for example a feeder, fence or housing structure. In some aspects, attachment element AE can comprise a slit through material 22, a grommet, a hook molded or formed into material 22, or a loop extending from a surface of material 22. The securing element can comprise a wire, string, hook, snap, button, zip-tie, or any other material suitable for engaging attachment element AE and attaching to an element to which an animal comes into contact.

Figure 3:
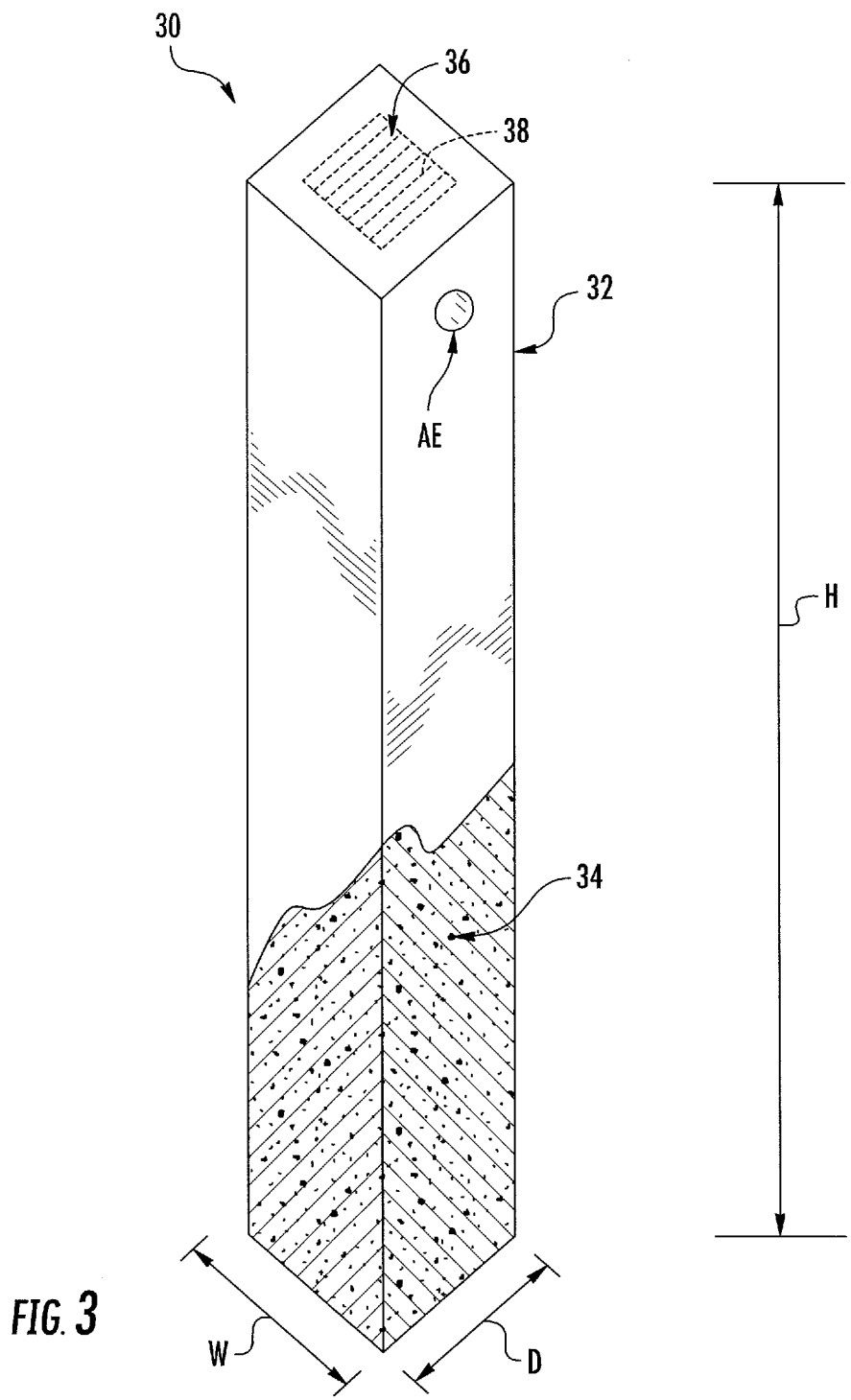
FIG. 3 is a perspective view, with partial cut-away view, of an elongated polygon embodiment of an apparatus in accordance with the subject matter herein.

FIG. 3 depicts an embodiment of an apparatus 30 configured to administer or emit an insecticidal compound for controlling or managing insect pests and/or ectoparasites on and/or around livestock animals, domesticated animals and humans. Apparatus 30 can in some embodiments comprise a material 32 capable of absorbing, or being impregnated with, an insecticidal compound 34. In some embodiments, material 32 can comprise a polyvinylchloride (PVC), polycarbonate, plastic, composite or other material suitable for absorbing an insecticidal compound 34. In some embodiments, material 32 can be in the shape of an elongated polygon structure, e.g. an elongated member with a cross section that is substantially square, rectangular or triangular, as depicted in FIG. 3. In some embodiments, material 32 in the shape of an elongated polygon having a depth D, or thickness, of about ½ inch to about 4 inches, a width W of about ½ inch to about 4 inches, and a height H, or length, of about 4 inches to about 36 inches. In some embodiments, material 32 in the shape of an elongated polygon can have a depth D, or thickness, of about ½ inch, about ¾ inch, about 1 inch, about 1½ inches, about 2 inches, about 2½ inches, about 3 inches, about 3½ inches, or about 4 inches, a width W of about ½ inch, about ¾ inch, about 1 inch, about 1½ inches, about 2 inches, about 2½ inches, about 3 inches, about 3½ inches, or about 4 inches, and a height H, or length, of about 4 inches, about 5 inches, about 6 inches, about 7 inches, about 8 inches, 9 inches, about 10 inches, about 12 inches, about 18 inches, about 24 inches, about 30 inches, or about 36 inches.

Continuing with FIG. 3, in some aspects insecticidal compound 34 is absorbed into at least a portion of material 32. In some aspects, material 32 of apparatus 30 can be impregnated with insecticidal compound 34 as depicted in the partial cut-away view. In some embodiments, material 32 can comprise a polyvinylchloride (PVC), polycarbonate, plastic, composite or other material capable of absorbing such a compound 34, or capable of being impregnated with compound 34. In some embodiments, insecticidal compound 34 can be impregnated into material 32 by mixing insecticidal compound 34 with material 32 prior to the molding of apparatus 30, following by a baking and/or curing procedure to thereby impregnate material 32 with insecticidal compound 34. In some aspects, apparatus 30 can be made from material 32 by way of molding, such as injection molding, to form the desired shape or configuration.

In some embodiments, insecticidal compound 34 can be administered to an animal or subject that comes into contact with apparatus 30 by virtue of the insecticidal compound 34 transferring to, or rubbing off of apparatus 30 and onto, the animal or subject upon contact between the animal or subject and a surface of apparatus 30. In some aspects, insecticidal compound 34 absorbed into material 32 can migrate to one or more surfaces of apparatus 30, whereby insecticidal compound 34 is administered to an animal or subject that comes into contact with the one or more surfaces of apparatus 30. In some embodiments, insecticidal compound 34 at or near a surface of apparatus 30 can be emitted into the surrounding air by way of dissipation from apparatus 30. As such, in some embodiment's apparatus 30 can provide for the control or treatment of insect pests and/or ectoparasites in a vicinity of apparatus 30, which can be placed or situated near livestock animals, domesticated animals and humans.

In some aspects, material 32 of apparatus 30 can be recharged or refilled with insecticidal compound 34 by allowing an insecticidal compound to be absorbed into material 32. In some aspects, apparatus 30 can be soaked in, dipped in, or otherwise exposed to an insecticidal compound 34, particularly in liquid form, to thereby recharge or refill an apparatus 30. In some aspects, material 32 of apparatus 30 can comprise a refillable region 36 where insecticidal compound 34 can be poured, applied, or otherwise administered to thereby recharge apparatus 30 with insecticidal compound 34. In some embodiments, refillable region 36 can comprise a center region of material 22, exposed at one or more surface or ends of apparatus 30 as depicted in FIG. 3. In some aspects, refillable region 36 can comprise an absorbent material 38. In some aspects, insecticidal compound 34 within refillable region 36 can migrate through material 32 to a surface of apparatus 30 such that it is positioned to dissipate into a space surrounding apparatus 30 or be administered to a subject or animal coming into contact with apparatus 30. In some embodiments, apparatus 30 can comprise a color agent, or indicator compound, that fades or changes color as the insecticide compound dissipates or is otherwise used up. Such an indicator compound can indicate to a user that apparatus 30 needs to be changed or recharged in order to maintain a desired insecticidal activity.

In some embodiments, apparatus 30 can comprise an attachment element AE for attaching apparatus 30 to an element to which an animal comes into contact. In some aspects, attachment element AE comprises a hole in material 32, as depicted in FIG. 3, through which a securing element can pass to thereby attach the apparatus to an element to which an animal comes into contact, such as for example a feeder, fence or housing structure. In some aspects, attachment element AE can comprise a slit through material 32, a grommet, a hook molded or formed into material 32, or a loop extending from a surface of material 32. The securing element can comprise a wire, string, hook, snap, button, zip-tie, or any other material suitable for engaging attachment element AE and attaching to an element to which an animal comes into contact.

Figure 4:
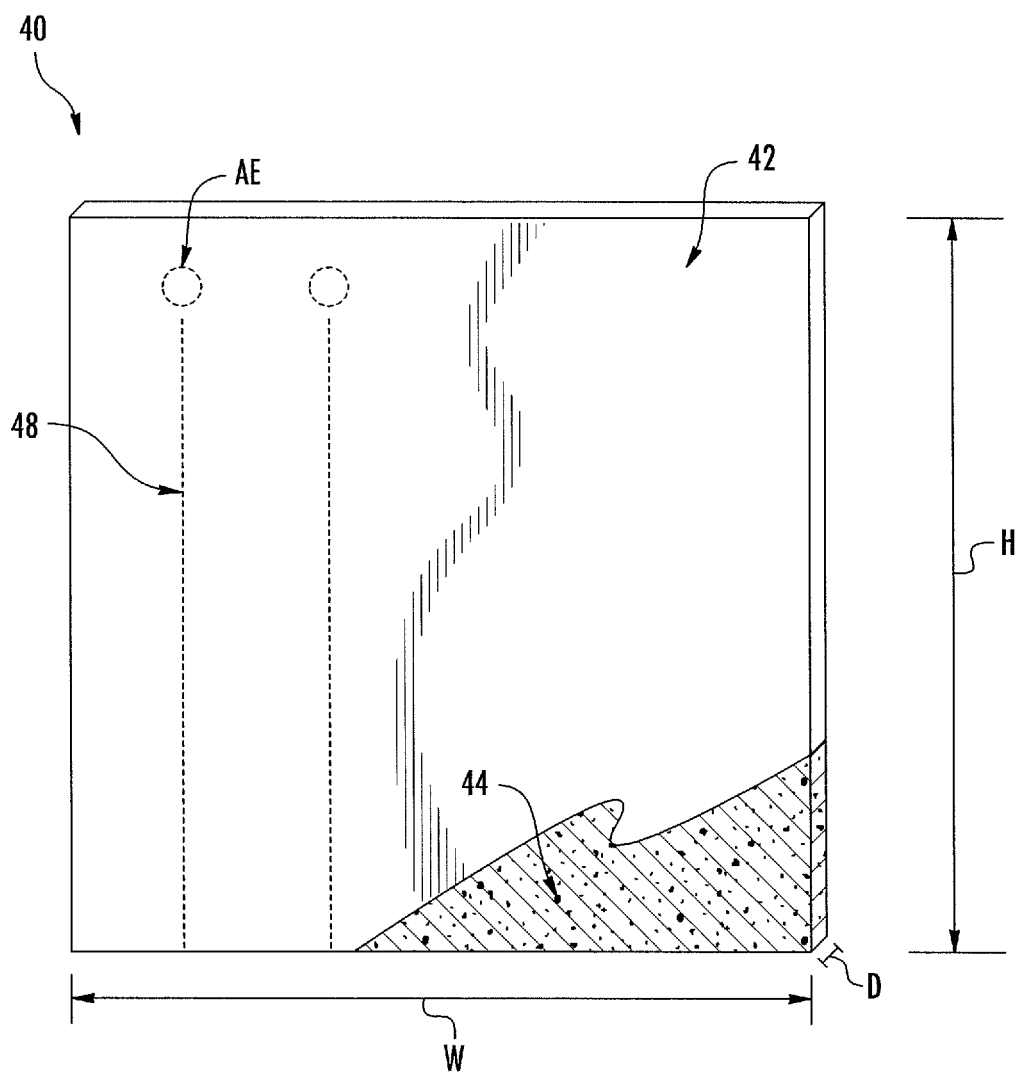
FIG. 4 is a perspective view, with partial cut-away view, of a sheet embodiment of an apparatus in accordance with the subject matter herein.

FIG. 4 depicts an embodiment of an apparatus 40 configured to administer or emit an insecticidal compound for controlling or managing insect pests and/or ectoparasites on and/or around livestock animals, domesticated animals and humans. Apparatus 40 can in some embodiments comprise a material 42 capable of absorbing, or being impregnated with, an insecticidal compound 44. In some embodiments, material 42 can comprise a polyvinylchloride (PVC), polycarbonate, plastic, composite or other material suitable for absorbing an insecticidal compound 44. In some embodiments, material 42 can be in the shape of a sheet, flap or substantially planar structure, as depicted in FIG. 4. In some embodiments, material 42 in the shape of a sheet can have a depth D, or thickness, of about $1/16^{th}$ inch to about 1 inch, a width W of about ½ inch to about 24 inches, and a height H, or length, of about 4 inches to about 36 inches. In some embodiments, material 42 in the shape of a sheet can have a depth D, or thickness, of about $1/16^{th}$ inch, about $1/8^{th}$ inch, about ¼ inch, about ½ inch, about ¾ inch, or about 1 inch, a width W of about ½ inch, about ¾ inch, about 1 inch, about 1½ inches, about 2 inches, about 2½ inches, about 3 inches, about 3½ inches, about 4 inches, about 5 inches, about 6 inches, about 7 inches, about 8 inches, 9 inches, about 10 inches, about 12 inches, about 18 inches, or about 24 inches, and a height H, or length, of about 4 inches, about 5 inches, about 6 inches, about 7 inches, about 8 inches, 9 inches, about 10 inches, about 12 inches, about 18 inches, about 24 inches, about 30 inches, or about 36 inches.

Continuing with FIG. 4, in some aspects insecticidal compound 44 is absorbed into at least a portion of material 42. In some aspects, material 42 of apparatus 40 can be impregnated with insecticidal compound 44 as depicted in the partial cut-away view. In some embodiments, material 42 can comprise a polyvinylchloride (PVC), polycarbonate, plastic, composite or other material capable of absorbing such a compound 44, or capable of being impregnated with compound 44. In some embodiments, insecticidal compound 44 can be impregnated into material 42 by mixing insecticidal compound 44 with material 42 prior to the molding of apparatus 40, following by a baking and/or curing procedure to thereby impregnate material 42 with insecticidal compound 44. In some aspects, apparatus 40 can be made from material 42 by way of molding, such as injection molding, to form the desired shape or configuration.

In some embodiments, insecticidal compound 44 can be administered to an animal or subject that comes into contact with apparatus 40 by virtue of the insecticidal compound 44 transferring to, or rubbing off of apparatus 40 and onto, the animal or subject upon contact between the animal or subject and a surface of apparatus 40. In some aspects, insecticidal compound 44 absorbed into material 42 can migrate to one or more surfaces of apparatus 40, whereby insecticidal compound 44 is administered to an animal or subject that comes into contact with the one or more surfaces of apparatus 40. In some embodiments, insecticidal compound 44 at or near a surface of apparatus 40 can be emitted into the surrounding air by way of dissipation from apparatus 40. As such, in some embodiment's apparatus 40 can provide for the control or treatment of insect pests and/or ectoparasites in a vicinity of apparatus 40, which can be placed or situated near livestock animals, domesticated animals and humans.

In some aspects, material 42 of apparatus 40 can be recharged or refilled with insecticidal compound 44 by allowing an insecticidal compound to be absorbed into material 42. In some aspects, apparatus 40 can be soaked in, dipped in, or otherwise exposed to an insecticidal compound 44, particularly in liquid form, to thereby recharge or refill an apparatus 40. In some embodiments, apparatus 40 can comprise a color agent, or indicator compound, that fades or changes color as the insecticide compound dissipates or is otherwise used up. Such an indicator compound can indicate to a user that apparatus 40 needs to be changed or recharged in order to maintain a desired insecticidal activity.

In some embodiments, apparatus 40 can comprise an attachment element AE for attaching apparatus 40 to an element to which an animal comes into contact. In some aspects, attachment element AE comprises a hole, or a plurality of holes in material 42, as depicted in FIG. 4, through which a securing element can pass to thereby attach the apparatus to an element to which an animal comes into contact, such as for example a feeder, fence or housing structure. In some aspects, attachment element AE can comprise one or more slits through material 42, grommets, hooks molded or formed into material 42, or loops extending from a surface of material 42. The securing element can comprise a wire, string, hook, snap, button, zip-tie, or any other material suitable for engaging attachment element AE and attaching to an element to which an animal comes into contact.

In some aspects apparatus 40 can optionally comprise one or more vertical cuts or breaks extending a partial length of the sheet-like structure of material 42, thereby forming a plurality of strips within the sheet of material 42, as depicted in FIG. 4. Such a configuration can allow for accessibility of an opening of a feeder by an animal when apparatus 40 is used in conjunction with a feeder to control insect pests and ectoparasites in an animal. Such an embodiment is illustrated in FIGS. 6B-6D, as discussed further hereinbelow.

Figure 5:
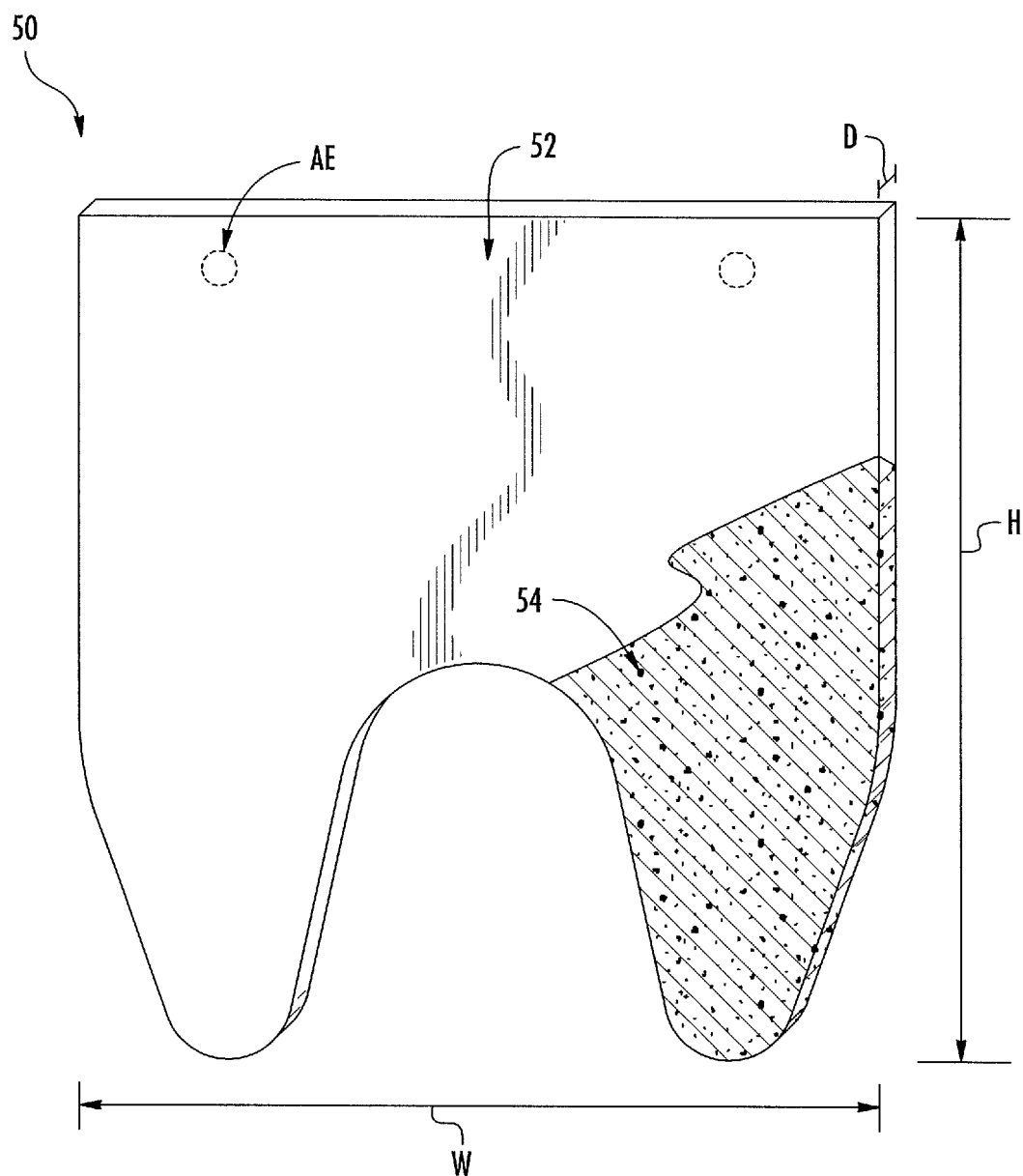
FIG. 5 is a perspective view, with partial cut-away view, of an alternate sheet embodiment of an apparatus in accordance with the subject matter herein.

FIG. 5 depicts an embodiment of an apparatus 50 configured to administer or emit an insecticidal compound for controlling or managing insect pests and/or ectoparasites on and/or around livestock animals, domesticated animals and humans. Apparatus 50 can in some embodiments comprise a material 52 capable of absorbing, or being impregnated with, an insecticidal compound 54. In some embodiments, material 52 can comprise a polyvinylchloride (PVC), polycarbonate, plastic, composite or other material suitable for absorbing an insecticidal compound 54. In some embodiments, material 52 can be in the shape of a sheet, flap or substantially planar structure, as depicted in FIG. 4. In some embodiments, material 52 in the shape of a sheet can have a depth D, or thickness, of about $1/16^{th}$ inch to about 1 inch, a width W of about ½ inch to about 24 inches, and a height H, or length, of about 4 inches to about 36 inches. In some embodiments, material 52 in the shape of a sheet can have a depth D, or thickness, of about $1/16^{th}$ inch, about $1/8^{th}$ inch, about ¼ inch, about ½ inch, about ¾ inch, or about 1 inch, a width W of about ½ inch, about ¾ inch, about 1 inch, about 1½ inches, about 2 inches, about 2½ inches, about 3 inches, about 3½ inches, about 4 inches, about 5 inches, about 6 inches, about 7 inches, about 8 inches, 9 inches, about 10 inches, about 12 inches, about 18 inches, or about 24 inches, and a height H, or length, of about 4 inches, about 5 inches, about 6 inches, about 7 inches, about 8 inches, 9 inches, about 10 inches, about 12 inches, about 18 inches, about 24 inches, about 30 inches, or about 36 inches.

Continuing with FIG. 5, in some aspects insecticidal compound 54 is absorbed into at least a portion of material 52. In some aspects, material 52 of apparatus 50 can be impregnated with insecticidal compound 54 as depicted in the partial cut-away view. In some embodiments, material 52 can comprise a polyvinylchloride (PVC), polycarbonate, plastic, composite or other material capable of absorbing such a compound 54, or capable of being impregnated with compound 54. In some embodiments, insecticidal compound 54 can be impregnated into material 52 by mixing insecticidal compound 54 with material 52 prior to the molding of apparatus 50, following by a baking and/or curing procedure to thereby impregnate material 52 with insecticidal compound 54. In some aspects, apparatus 50 can be made from material 52 by way of molding, such as injection molding, to form the desired shape or configuration.

In some embodiments, insecticidal compound 54 can be administered to an animal or subject that comes into contact with apparatus 50 by virtue of the insecticidal compound 54 transferring to, or rubbing off of apparatus 50 and onto, the animal or subject upon contact between the animal or subject and a surface of apparatus 50. In some aspects, insecticidal compound 54 absorbed into material 52 can migrate to one or more surfaces of apparatus 50, whereby insecticidal compound 54 is administered to an animal or subject that comes into contact with the one or more surfaces of apparatus 50. In some embodiments, insecticidal compound 54 at or near a surface of apparatus 50 can be emitted into the surrounding air by way of dissipation from apparatus 50. As such, in some embodiment's apparatus 50 can provide for the control or treatment of insect pests and/or ectoparasites in a vicinity of apparatus 50, which can be placed or situated near livestock animals, domesticated animals and humans.

In some aspects, material 52 of apparatus 50 can be recharged or refilled with insecticidal compound 54 by allowing an insecticidal compound to be absorbed into material 52. In some aspects, apparatus 50 can be soaked in, dipped in, or otherwise exposed to an insecticidal compound 54, particularly in liquid form, to thereby recharge or refill an apparatus 50. In some embodiments, apparatus 50 can comprise a color agent, or indicator compound, that fades or changes color as the insecticide compound dissipates or is otherwise used up. Such an indicator compound can indicate to a user that apparatus 50 needs to be changed or recharged in order to maintain a desired insecticidal activity.

In some embodiments, apparatus 50 can comprise an attachment element AE for attaching apparatus 50 to an element to which an animal comes into contact. In some aspects, attachment element AE comprises a hole, or a plurality of holes in material 52, as depicted in FIG. 5, through which a securing element can pass to thereby attach the apparatus to an element to which an animal comes into contact, such as for example a feeder, fence or housing structure. In some aspects, attachment element AE can comprise one or more slits through material 52, grommets, hooks molded or formed into material 52, or loops extending from a surface of material 52. The securing element can comprise a wire, string, hook, snap, button, zip-tie, or any other material suitable for engaging attachment element AE and attaching to an element to which an animal comes into contact.

Although not depicted in FIG. 5, in some aspects apparatus 50 can optionally comprise one or more vertical cuts or breaks extending a partial length of the sheet-like structure of material 52, thereby forming a plurality of strips within the sheet of material 52, as depicted in FIG. 4. In some embodiments, the sheet-like structure of material 52 of apparatus 50 can have an ergonomic shape, on at least a portion of the sheet-like structure of material 52, substantially matching the shape of an animal's head or neck when in contact with apparatus 50. Such a configuration can allow for accessibility of an opening of a feeder by an animal when apparatus 50 is used in conjunction with a feeder to control insect pests and ectoparasites in an animal. Such an embodiment is illustrated in FIGS. 6C-6D, as discussed further hereinbelow.

Figure 6A:
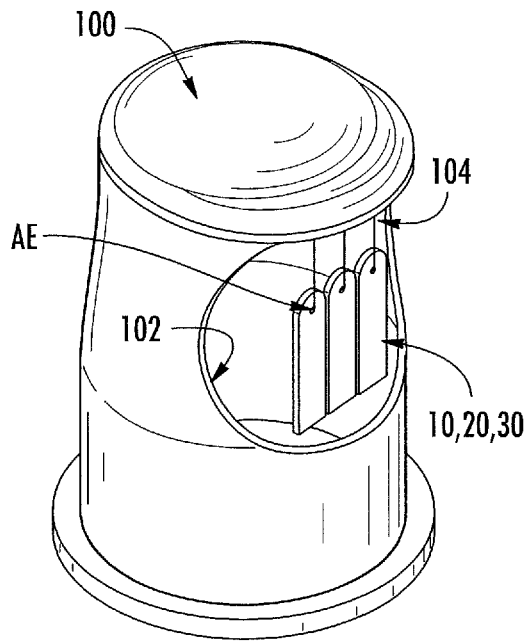
FIG. 6A is a perspective view of a livestock feeder illustrating the use an elongated strip, cylinder or polygon embodiment of the apparatus in conjunction with a feeder.
Figure 6B:
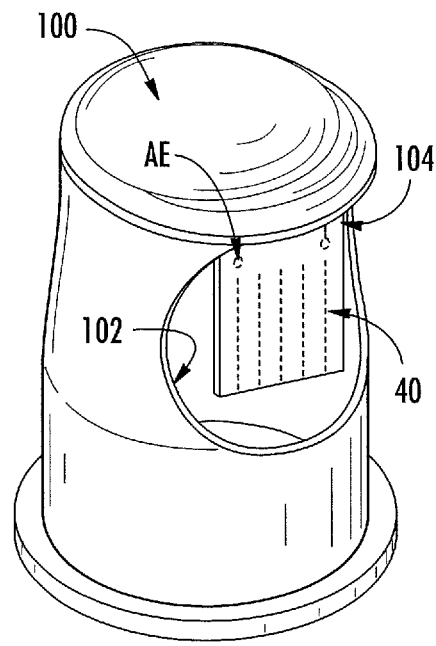
FIG. 6B is a perspective view of a livestock feeder illustrating the use a sheet embodiment of the apparatus in conjunction with a feeder.
Figure 6C:
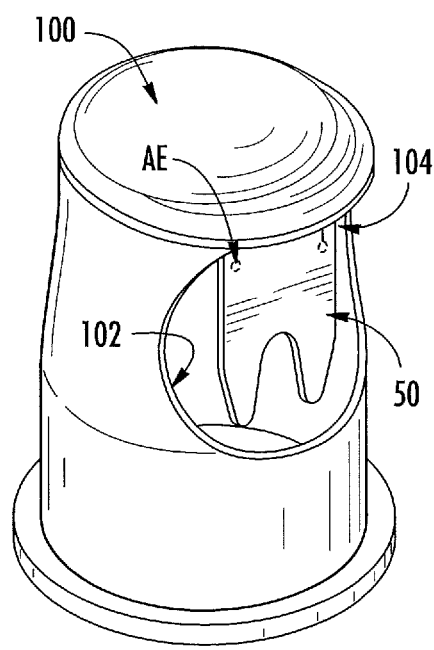
FIG. 6C is a perspective view of a livestock feeder illustrating the use an alternate sheet embodiment of the apparatus in conjunction with a feeder.
Figure 6D:
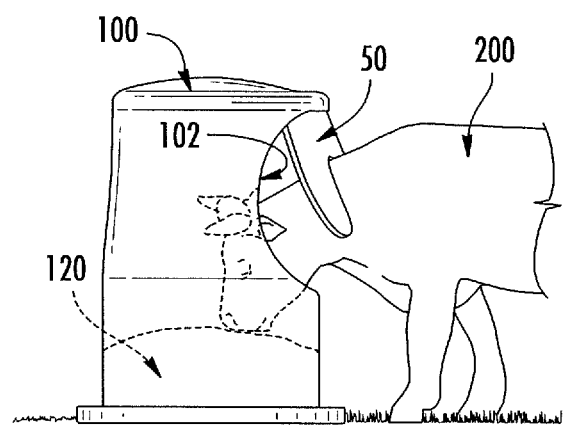
FIG. 6D is a side and partial cut-away view of a livestock feeder illustrating the feeder and sheet apparatus in use.

FIG. 6A is a perspective view of a livestock feeder 100 illustrating the use an apparatus 10, 20 and/or 30, the elongated strip, elongated cylinder and elongated polygon embodiments, respectively, in conjunction with a livestock feeder 100. In some embodiments a feeder 100 can comprise a feeder such as that disclosed in U.S. patent application Ser. No. 13/188,173, herein incorporated by reference in its entirety. In some embodiments, an apparatus 10, 20 and/or 30 can be placed in an opening 102 within the feeder through which an animal can access a feedstuff within the feeder 102. In this manner apparatus 10, 20 and/or 30 can be used to apply insecticidal compounds to an animal while the animal is using the feeder 102. One or more of apparatus 10, 20 and/or 30 can be positioned at or near the opening 102 of the feeder 100 so that the animal will come into contact with an apparatus 10, 20 and/or 30 upon accessing the feeder 100 through the opening 102. In some aspects, one, two, three, four, five, six, seven, eight, nine, ten, or more of apparatus 10, 20 and/or 30 can be positioned at or near the opening 102 of the feeder 100. When the animal makes contact with or brushes up against an apparatus 10, 20 and/or 30 the insecticidal compound will rub off on the animal. In some embodiments, one or more apparatus 10, 20 and/or 30 can be secured near the top of opening 102, as illustrated in FIG. 6A, using attachment element AE of apparatus 10, 20 and/or 30 and a fastening device 104. Fastening device 104 can in some embodiments comprise a hook, bolt, screw, snap, rivet or other fastening device suitable for engaging attachment element AE on apparatus 10, 20 and/or 30.

FIG. 6B is a perspective view of a livestock feeder 100 illustrating the use an apparatus 40, the sheet, flap or substantially planar structure embodiment, in conjunction with a livestock feeder 100. In some embodiments, apparatus 40 can be placed in an opening 102 within the feeder through which an animal can access a feedstuff within the feeder 102. In this manner apparatus 40 can be used to apply insecticidal compounds to an animal while the animal is using the feeder 102. One or more of apparatus 40 can be positioned at or near the opening 102 of the feeder 100 so that the animal will come into contact with apparatus 40 upon accessing the feeder 100 through the opening 102. When the animal makes contact with or brushes up against apparatus 40 the insecticidal compound will rub off on the animal. In some embodiments, an apparatus 40 can be secured near the top of opening 102, as illustrated in FIG. 6B, using attachment element AE of apparatus 40 and a fastening device 104. Fastening device 104 can in some embodiments comprise a hook, bolt, screw, snap, rivet or other fastening device suitable for engaging attachment element AE on apparatus 40. In some embodiments, apparatus 40 can substantially cover opening 102 to thereby provide an additional advantage by preventing, reducing or minimizing precipitation from entering opening 102 to thereby keep feedstuffs in feeder 100 dry. Apparatus 40 can in some embodiments be a clear, opaque or tinted material. Apparatus 40 can be designed to allow livestock ready access to the feedstuffs in feeder 100 while protecting the feedstuffs from environmental elements.

FIG. 6C is a perspective view of a livestock feeder 100 illustrating the use an apparatus 50, the alternative sheet, flap or substantially planar structure embodiment with an ergonomic shape, in conjunction with a livestock feeder 100. In some embodiments, apparatus 50 can be placed in an opening 102 within the feeder through which an animal can access a feedstuff within the feeder 102. In this manner apparatus 50 can be used to apply insecticidal compounds to an animal while the animal is using the feeder 102. One or more of apparatus 50 can be positioned at or near the opening 102 of the feeder 100 so that the animal will come into contact with apparatus 50 upon accessing the feeder 100 through the opening 102. When the animal makes contact with or brushes up against apparatus 50 the insecticidal compound will rub off on the animal. In some embodiments, an apparatus 50 can be secured near the top of opening 102, as illustrated in FIG. 6C, using attachment element AE of apparatus 50 and a fastening device 104. Fastening device 104 can in some embodiments comprise a hook, bolt, screw, snap, rivet or other fastening device suitable for engaging attachment element AE on apparatus 50. In some embodiments, apparatus 50 can substantially cover opening 102 to thereby provide an additional advantage by preventing, reducing or minimizing precipitation from entering opening 102 to thereby keep feedstuffs in feeder 100 dry. Apparatus 50 can in some embodiments be a clear, opaque or tinted material. Apparatus 50 can be designed to allow livestock ready access to the feedstuffs in feeder 100 while protecting the feedstuffs from environmental elements.

FIG. 6D is a side and partial cut-away view of a livestock feeder 100 illustrating the feeder 100 and apparatus 50, for example, in use. Though not illustrated here, apparatus 10, 20, 30 or 40 would operate similarly when in use. As illustrated in FIG. 6D, when animal 200 enters feeder 100 through opening 102 to access feed 120, the animal 200 comes into contact with apparatus 50. When animal 200 makes contact with or brushes up against apparatus 50 the insecticidal compound will rub off on animal 200, thereby providing a treatment for, or otherwise controlling or managing one or more insect, pest or parasite populations affecting animal 200.

Figure 7:
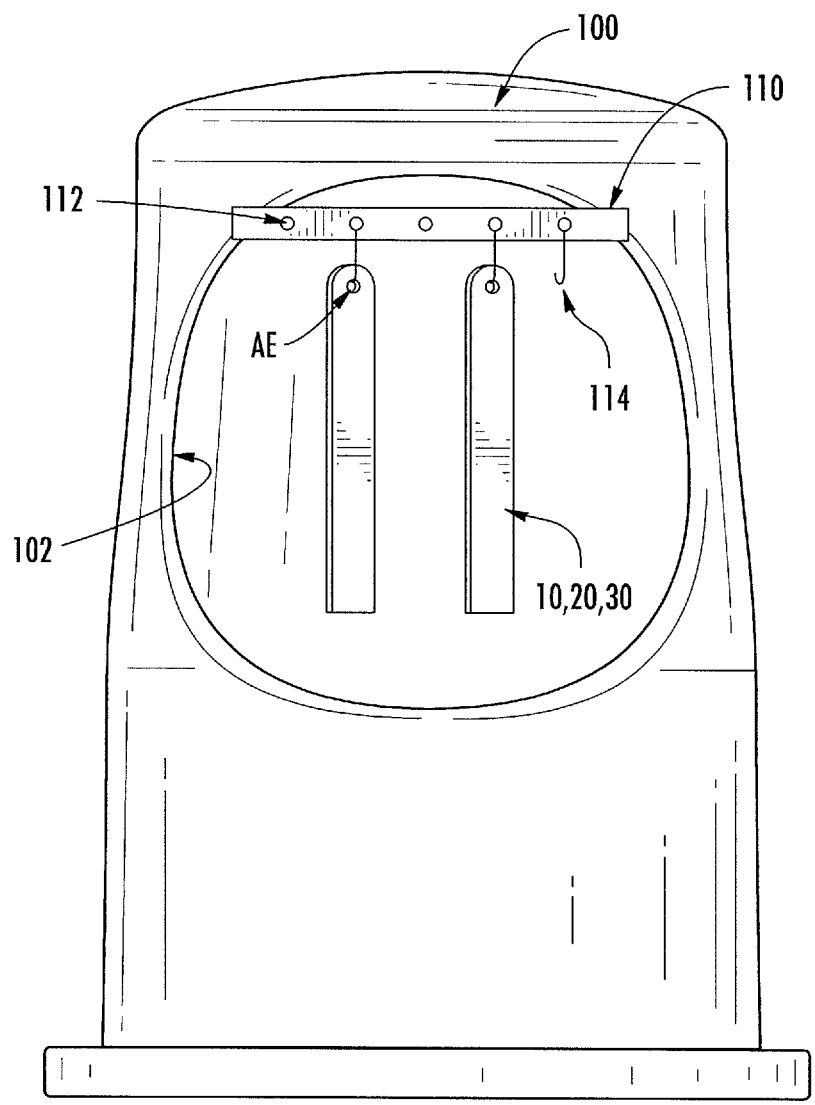
FIG. 7 is a front view of a livestock feeder illustrating embodiments of the apparatus in use with an attachment base.

FIG. 7 is a front view of a livestock feeder 100 illustrating embodiments of an apparatus 10, 20, 30 in use with an attachment base 110. For illustration purposes only, apparatus 10, 20, 30 is shown in FIG. 7, but apparatus 40 or 50 can be used with an attachment base 110 in a similar manner. Attachment base 100 can in some embodiments comprise a substantially planar structure or strip of material, e.g. a plastic, composite, PVC, aluminum, metal, fiberglass or the like, that is configured to be secured to or otherwise attached to an element to which an animal comes into contact. In some embodiments, attachment base 110 can comprise a semi-circular shape, or half-moon shape, to accommodate the opening of a feeder 100. Attachment base 110 can comprise any desired shape or configuration depending on the element to which it is to be attached, and provided it provides a mechanism to secure or otherwise attach an insecticidal apparatus as disclosed herein.

Attachment base 110 can be configured to be attached to an element to which an animal comes into contact, such as for example a feeder (depicted in FIG. 7), fence, or housing structure. In some aspects, attachment base 110 can have a substantially straight and rectangular configuration, as depicted in FIG. 7, or can be curved or ergonomically shaped to fit an opening of a feeder or other element. Attachment base 110 can be secured to feeder 100, or any other element, using any suitable means of attachment, including for example, screws, nails, rivets, bolts and/or adhesive.

In some embodiments, attachment base 110 can comprise one or more openings 112 through which a securing material, e.g. wire, string, rope, twine or zip-ties, can be used to attach an apparatus 10, 20, 30 using attachment element AE of apparatus 10, 20, 30. In some aspects, attachment base 110 can comprise one or more fastening devices 114. Fastening device 114 can in some embodiments comprise a hook, bolt, screw, snap, rivet or other fastening device suitable for engaging attachment element AE on apparatus 10, 20, 30.

In some embodiments, an insect pest control kit is provided. An insect pest control kit can in some embodiments comprise an apparatus for administering an insecticidal compound to an animal, and an attachment base configured to be attached to an element to which an animal comes into contact, wherein the apparatus is attachable to the attachment base by way of the attachment element. The apparatus for administering an insecticidal compound can comprise a material for absorbing an insecticidal compound, an insecticidal compound, wherein the insecticidal compound is absorbed into at least a portion of the material, and an attachment element, wherein the insecticidal compound is capable of being administered to an animal that comes into contact with the apparatus. In some aspects, the attachment base of the kit is configured to be attached to a feeder, fence, or housing structure.

For illustrative purposes only, an insecticidal apparatus is illustrated in use with a feeder in FIGS. 6A-6D and 7. In some embodiments, an insecticidal apparatus as disclosed herein can be strategically placed at any location or on any element where it will come into contact with the desired animal to be treated, e.g. feeders, water sources, fences, housing structures and handling facilities.

In some aspects, an insecticidal apparatus as disclosed herein comprises an insecticidal compound comprising an anti-parasitic compound, an insecticide, an ectoparasiticide, or combinations thereof. By way of example and not limitation, the insecticidal compound can be selected from the group consisting of organochlorines, organophosphates, carbamates, pyrethrins, pyrethroids, avermectins, milbemycins, formamidines, insect growth regulators, synergists, MGK-264, butoxypolypropylene-glycol, and DEET. By way of example and not limitation, the insecticidal compound is effective against lice, keds, mites, ticks, flies, horn flies, stable flies, horse flies, mosquitos, face flies, house flies, blowflies, both on or around animals (livestock and domesticated) and humans. In some aspects, the insecticidal compound is effective against borers, termites, wood destroying insects, ants, spiders, moths, fleas, bed bugs, mosquitoes, gnats, biting flies, house flies no-see-urns, ticks, and deer ticks, both in and around animals and humans and their surroundings, e.g. homes and buildings.

In some embodiments, an insecticidal compound in an apparatus as disclosed herein can comprise an ectoparasiticide. As described in the Merck Veterinary Manual ($10^{th}$ Edition, 2010) arthropod parasites (ectoparasites) are a major cause of production losses in livestock throughout the world. In addition, many arthropod species act as vectors of disease for both animals and humans. Treatment with various drugs to reduce or eliminate ectoparasites is therefore often required to maintain health and to prevent economic loss in food animals. The choice and use of ectoparasiticides depends to a large extent on husbandry and management practices, as well as on the type of ectoparasite causing the infestation. Accurate identification of the parasite or correct diagnosis based on clinical signs is necessary for selection of the appropriate drug. The selected agent can be administered or applied directly to the animal, or introduced into the environment to reduce the arthropod population to a level that is no longer of economic or health consequence.

Parasites that live permanently on the skin, such as lice, keds, and mites, are controlled by directly treating the host. Some mange mites burrow into the skin and are therefore more difficult to control with sprays or dips than are lice and keds, which are found on the surface of the skin. However, once these obligate parasites are eradicated, reinfection occurs only from contact with other infected animals. Nonpermanent parasites (ticks, flies, etc) are less easily controlled because only a small proportion of the population can be treated at any one time, and other hosts may maintain them. Some tick and mite species stay on the host only long enough to feed, which may be as short as 30 min, or as long as 21 days. Biting flies, such as the horn fly, can be found continuously on the backs and undersides of cattle, where they suck blood up to 20 times a day; other biting flies (such as stable flies and horse flies) and mosquitos feed to repletion, then leave the animal to lay eggs. Nonbiting flies, such as the face fly or the house fly, may visit infrequently but can be very annoying and may transmit disease agents. Larvae of certain blowflies live on the skin or in tissues of sheep and other animals and cause cutaneous myiasis. Larvae of other flies spend several months inside animals, e.g., nasal bots in the nasal passages of sheep and goats, bots in the stomach of horses, and cattle grubs or warbles in the spinal canal, back, or esophageal tissues.

Many ectoparasite infestations are seasonal and predictable and can be countered by prophylactic use of ectoparasiticides. For example, in temperate countries flies are seen predominantly from late spring to early autumn, tick populations increase in the spring and autumn, and lice and mites during the autumn and winter months. Treatments can therefore be targeted at anticipated times of peak activity as a means of limiting disease and parasite populations.

In some embodiments, an ectoparasiticide used in the presently disclosed subject matter can comprise a chemotherapeutic agent. Most ectoparasiticides are neurotoxins, exerting their effect on the nervous system of the target parasite. Those used in large animals can be grouped according to structure and modes of action into the organochlorines, organophosphates and carbamates, pyrethrins and pyrethroids (including Permethrin), avermectins and milbemycins, formamidines, insect growth regulators, and a number of miscellaneous compounds, including synergists (e.g., piperonyl butoxide). There are also a number of useful compounds that have repellent activity rather than insecticidal activity, including MGK-264, butoxypolypropyleneglycol, and DEET.

In some embodiments, an ectoparasiticide used in the presently disclosed subject matter can comprise an organochlorine. Organochlorine compounds have been withdrawn in many parts of the world due to concerns regarding environmental persistence. However, some compounds, including lindane (γ benzene hexachloride) and methoxychlor, are still used for topical application and have excellent activity and apparent safety.

Organochlorines fall into 3 main groups: 1) chlorinated ethane derivatives such as DDT (dichlorodiphenyltrichloroethane), DDE (dichlorodiphenyldichloroethane), and DDD (dicofol, methoxychlor); 2) cyclodienes, including chlordane, aldrin, dieldrin, hepatochlor, endrin, and tozaphene; and 3) hexachlorocyclohexanes such as benzene hexachloride (BHC), which includes the g-isomer, lindane.

Chlorinated ethanes cause inhibition of sodium conductance along sensory and motor nerve fibers by holding sodium channels open, resulting in delayed repolarization of the axonal membrane. This state renders the nerve vulnerable to repetitive discharge from small stimuli that would normally cause an action potential in a fully repolarized neuron.

The cyclodienes appear to have at least 2 component modes of action-inhibition of γ-amino butyric acid (GABA)-stimulated Cl flux and interference with $Ca^{2+}$ flux. The resultant inhibitory postsynaptic potential leads to a state of partial depolarization of the postsynaptic membrane and vulnerability to repeated discharge. A similar mode of action has been reported for lindane, which binds to the picrotoxin side of GABA receptors, resulting in an inhibition of GABA-dependent Cl flux into the neuron.

DDT and BHC were used extensively for flystrike control but were subsequently replaced in many countries by more effective cyclodiene compounds, such as dieldrin and aldrin. The development of resistance, as well as environmental concerns, have largely led to their withdrawal. DDT and lindane were widely used in dip formulations for the control of sheep scab, but the organophosphates and subsequently the synthetic pyrethroids have mostly replaced them.

In some embodiments, an ectoparasiticide used in the presently disclosed subject matter can comprise an organophosphate and/or carbamate. The organophosphates comprise a large group, many of which are available for topical application and in ear tags as well as for premise control of parasites. There have been many products available worldwide for use in domestic animals, although only a few of the available compounds continue to be used for on-animal treatment.

Organophosphates are neutral esters of phosphoric acid or its thio analog that inhibit the action of acetylcholinesterase (AChE) at cholinergic synapses and at muscle endplates. The compound mimics the structure of acetylcholine (ACh); when it binds to AChE it causes transphosphorylation of the enzyme. The transphorylated AChE is unable to break down accumulating ACh at the postsynaptic membrane, leading to neuromuscular paralysis. The degree of transphorylation of the enzyme helps to determine the activity of the organophosphate. This is not an irreversible process; eventually the AChE is metabolized by oxidative and hydrolytic enzyme systems.

Organophosphates can be extremely toxic in animals and humans, causing an inhibition of AChE and other cholinesterases. Chronic toxicity results from inhibition of the enzyme neurotoxic esterase and is associated with particular compounds. The physiologic function of this enzyme is unknown; however, its inhibition appears to cause structural changes in neuronal membranes and a reduction in conduction velocity, which may be manifest as posterior paralysis in some animal species. Cases of organophosphate toxicity are treated with oximes or atropine.

Organophosphates used topically include coumaphos, diazinon, dichlorvos, famphur, fenthion, malathion, trichlorfon, stirofos, phosmet, and propetamphos. Ear tags containing fenthion, chlorpyrifos, and diazinon are available in some countries. These compounds are generally active against fly larvae, flies, lice, ticks, and mites on domestic livestock, although activity varies between compounds and differing formulations. Chlorpyrifos is best used in the microencapsulated form for residual activity and improved safety. Diazinon and propetamphos have been available in dip formulations for the control of psoroptic mange in sheep. Both eliminate mites and protect in a single application when correctly applied. Diazinon provides longer residual protection than propetamphos. In cattle, a number of compounds have been used for the systemic control of warble fly grubs and lice as pour-on applications or in hand sprays, spray races, or dips for tick control. Products containing haloxon and metriphonate have been used PO for the control of stomach bot fly larvae and helminths in horses.

Carbamate insecticides are closely related to organophosphates and are anticholinesterases. Unlike organophosphates, they appear to cause a spontaneously reversible block on AChE without changing it. The 2 main carbamate compounds used are carbaryl and propoxur. Carbaryl has low mammalian toxicity but may be carcinogenic and is often combined with other active ingredients. P In some embodiments, an ectoparasiticide used in the presently disclosed subject matter can comprise a pyrethrin and/or synthetic pyrethroid. A number of pyrethroids are available in many countries as pour-on, spot-on, spray, and dip formulations with activity against biting and nuisance flies, lice, and ticks on a domestic livestock. Flumethrin and high cis-cypermethrin are also active against mites and are used for the treatment of psoroptic mange of sheep.

Natural pyrethrins are derived from pyrethrum, a mixture of alkaloids from the chrysanthemum plant. Pyrethrum extract, prepared from pyrethrum flower, contains ~25% pyrethrins. The pyrethrins and pyrethroids are lipophilic molecules that generally undergo rapid absorption, distribution, and excretion. They provide excellent knockdown (rapid kill) but have poor residual activity due to instability. Pyrethrin I is the most active ingredient for kill, and pyrethrin II for rapid insect knockdown.

Synthetic pyrethroids, such as permethrin, are synthesized chemicals modeled on the natural pyrethrin molecule. They are more stable and have a higher potency than natural pyrethrins.

The mode of action of pyrethrins and synthetic pyrethroids appears to be interference with sodium channels of the parasite nerve axons, resulting in delayed repolarization and eventual paralysis. Synthetic pyrethroids can be divided into 2 groups (types I and II, depending on the presence or absence of an α-cyano moiety). Type I compounds have a mode of action (similar to that of DDT) that involves interference with the axonal $Na^+$ gate leading to delayed repolarization and repetitive discharge of the nerve. Type II compounds also act on the $Na^+$ gate but do so without causing repetitive discharge. The lethal activity of pyrethroids seems to involve action on both peripheral and central neurons, while the knockdown effect is probably produced by peripheral neuronal effects only. Some preparations contain piperonyl butoxide, which acts as a synergist by helping to prevent the pyrethrin or pyrethroid breakdown by microsomal mixed-function oxidase systems in insects.

Pyrethroids are generally safe in mammals and birds but are highly toxic to fish and aquatic invertebrates. Concerns have been expressed over their environmental effects, particularly in relation to the aquatic environment.

Some of the more common pyrethroids used include bioallethrin, cypermethrin, deltamethrin, fenvalerate, flumethrin, lambdacyhalothrin, phenothrin, and permethrin. The content of some synthetic pyrethroids is also expressed in terms of the drug isomers, e.g., cypermethrin preparations may contain varying proportions of their cis and trans isomers. Thus, cypermethrin (cis:trans 60:40) 2.5% is equivalent to cypermethrin (cis:trans 80:20) 1.25%. In general, cis isomers are more active than the corresponding trans isomers.

In some embodiments, an ectoparasiticide used in the presently disclosed subject matter can comprise a macrocyclic lactones (Avermectins and Milbemycins). Avermectins and the structurally related milbemycins, collectively referred to as macrocyclic lactones, are fermentation products of *Streptomyces avermilitis* and *Streptomyces cyanogriseus*, respectively. Avermectins differ from each other chemically in side chain substitutions on the lactone ring, while milbemycins differ from the avermectins through the absence of a sugar moiety from the lactone skeleton. A number of macrocyclic lactone compounds are available for use and include the avermectins abamectin, doramectin, eprinomectin, ivermectin, and selamectin, and the milbemycins moxidectin and milbemycin oxime. These compounds are active against a wide range of nematodes and arthropods and, as such, are often referred to as endectocides.

Endectocidal activity, particularly against ectoparasites, is variable and depends on the active molecule, the product formulation, and the method of application. Macrocyclic lactones can be given PO, parenterally, or topically (as pour-ons). The method of application depends on the host and, to some degree, on the target parasites. In cattle, e.g., available endectocide products can be given PO, by injection, or topically using pour-on formulations. The latter are generally more effective against lice (*Lignonathus, Haematopinus*, and to some extent *Bovicola*) and headfly (*Haematobia/Lyperosia*) infestations, when compared with equivalent compounds administered parenterally. In sheep, PO administration of some endectocides has little effect against psoroptic mite infestations (*Psoroptes ovis*), but parenteral administration increases activity.

The route of administration and product formulation all influence rates of absorption, metabolism, excretion, and subsequent bioavailability and pharmacokinetics of individual compounds. Avermectins and milbemycins are highly lipophilic, a property that varies with only minor modifications in molecular structure or configuration. Following administration, macrocyclic lactones are stored in fat, from which they are slowly released, metabolized, and excreted. Ivermectin is absorbed systemically following PO, SC, or dermal administration; it is absorbed to a greater degree and has a longer half-life when given SC or dermally. Excretion of the unaltered molecule is mainly via the feces, with <2% excreted in the urine in ruminants. In cattle, the reduced absorption and bioavailability of ivermectin given PO may be due to its metabolism in the rumen. The affinity of these compounds for fat explains their persistence in the body and the extended periods of protection afforded against some species of internal and external parasites. The prolonged half-life of these compounds also determines residue levels in meat and milk, and subsequent compulsory withdrawal periods following treatment in food-producing animals.

The mode of action of avermectins and milbemycins is still not completely understood. Ivermectin is known to act on GABA neurotransmission at 2 or more sites in nematodes, blocking interneuronal stimulation of excitatory motor neurons, leading to flaccid paralysis. It appears to achieve this by stimulating the release of GABA from nerve endings and by enhancing the binding of GABA to its receptor on the postsynaptic membrane of an excitatory motor neuron. The enhanced GABA binding results in an increased flow of $Cl^-$ ions into the cell, leading to hyperpolarization. In mammals, GABA neurotransmission is confined to the CNS; the lack of effect of ivermectin on mammalian nervous systems at therapeutic concentrations is probably because it does not readily cross the blood-brain barrier. More recent evidence suggests that ivermectin may exert its effect through action on glutamate-gated $Cl^-$ ion conductance at the postsynaptic membrane or neuromuscular endplate.

In some embodiments, an ectoparasiticide used in the presently disclosed subject matter can comprise a formamidine. Amitraz is the only formamidine used as an ectoparasiticide. It appears to act by inhibition of the enzyme monoamine oxidase and as an agonist at octopamine receptors. Monoamine oxidase metabolizes amine neurotransmitters in ticks and mites, and octopamine is thought to modify tonic contractions in parasite muscles. Amitraz has a relatively wide safety margin in mammals; the most frequently associated side effects include sedation, which may be associated with an agonist activity of amitraz on $α_2$-receptors in mammalian species.

Amitraz is available as a spray or dip for use against mites, lice, and ticks in domestic livestock. It is contraindicated in horses.

In some embodiments, an ectoparasiticide used in the presently disclosed subject matter can comprise a chloronicotinyl and/or Spinosyn. Imidacloprid is a chloronicotinyl insecticide, a synthesized chlorinated derivative of nicotine. Spinosad is a fermentation product of the soil actinomycete *Saccharopolyspora spinosa*. Both compounds bind to nicotinic acetylcholine receptors (but at different sites) in the insect's CNS, leading to inhibition of cholinergic transmission, paralysis, and death. Spinosad has been developed in some countries for use on sheep in the control of blowfly strike and lice.

In some embodiments, an ectoparasiticide used in the presently disclosed subject matter can comprise an insect growth regulator. Insect growth regulators are used throughout the world and represent a relatively new category of insect control agents. They constitute a group of chemical compounds that do not kill the target parasite directly, but interfere with growth and development. They act mainly on immature parasite stages and are not usually suitable for the rapid control of established adult parasite populations. Where parasites show a clear seasonal pattern, insect growth regulators can be applied prior to any anticipated challenge as a preventive measure. They are widely used for blowfly control in sheep but have limited use in other livestock.

Based on their mode of action, insect growth regulators can be divided into chitin synthesis inhibitors (benzoylphenyl ureas), chitin inhibitors (triazine/pyrimidine derivatives), and juvenile hormone analogs. Several benzoylphenyl ureas have been introduced for the control of ectoparasites. Chitin is a complex aminopolysaccharide and a major component of the insect's cuticle. During each molt, it has to be newly formed by polymerization of individual sugar molecules. The exact mode of action of the benzoylphenyl ureas is not fully understood. They inhibit chitin synthesis but have no effect on the enzyme chitin synthetase. It has been suggested that they interfere with the assembly of the chitin chains into microfibrils. When immature insect stages are exposed to these compounds, they are not able to complete ecdysis and die during molting. Benzoylphenyl ureas also appear to have a transovarial effect. Exposed adult female insects produce eggs in which the compound is incorporated into the egg nutrient. Egg development proceeds normally, but the newly developed larvae are incapable of hatching. Benzoylphenyl ureas show a broad spectrum of activity against insects but have relatively low efficacy against ticks and mites. The exception is fluazuron, which has greater activity against ticks and some mite species.

Benzoylphenyl ureas are highly lipophilic molecules. When administered to the host, they build up in body fat, from which they are slowly released into the bloodstream and excreted largely unchanged. Diflubenzuron and flufenoxuron are used for the prevention of blowfly strike in sheep. Diflubenzuron is available in some countries as an emulsifiable concentrate for use as a dip or shower. It is more efficient against first-stage larvae than second and third instars and is therefore recommended as a preventive, providing protection for 12-14 wk. It may also have potential for the control of a number of major insect pests such as tsetse flies. Fluazuron is available in some countries for use in cattle as a tick development inhibitor. When applied as a pour-on, it provides longterm protection against the 1-host tick *Boophilus microplus*.

Triazine and pyrimidine derivatives are closely related compounds that are also chitin inhibitors. They differ from the benzoylphenyl ureas both in chemical structure and mode of action, in that they appear to alter the deposition of chitin into the cuticle rather than its synthesis.

Cyromazine, a triazine derivative, is effective against blowfly larvae on sheep and lambs and also against other Diptera such as houseflies and mosquitos. At recommended dose rates, cyromazine shows only limited activity against established strikes and must therefore be used preventively. Blowflies usually lay eggs on damp fleece of treated sheep. Although larvae are able to hatch, the young larvae immediately come into contact with cyromazine, which prevents the molt to second instars. The efficacy of a pour-on preparation of cyromazine does not depend on factors such as weather, fleece length, and whether the fleece is wet or dry. Control can be maintained for up to 13 wk after a single pour-on application, or longer if cyromazine is applied by dip or shower.

Dicyclanil, a pyrimidine derivative, is highly active against dipteran larvae. A pour-on formulation, available in some countries for blowfly control in sheep, provides up to 20 wk of protection.

The juvenile hormone analogs mimic the activity of naturally occurring juvenile hormones and prevent metamorphosis to the adult stage. Once the larva is fully developed, enzymes within the insect's circulatory system destroy endogenous juvenile hormones, prompting development to the adult stage. The juvenile hormone analogs bind to juvenile hormone receptor sites, but because they are structurally different, are not destroyed by insect esterases. As a consequence, metamorphosis and further development to the adult stage does not proceed. Methoprene is a terpenoid compound with very low mammalian toxicity that mimics a juvenile insect hormone and is used as a feed-through larvicide for hornfly (*Haematobia*) control on cattle.

Piperonyl butoxide is a methylenedioxyphenyl compound that has been widely used as a synergistic additive in the control of arthropod pests. It is commonly used as a synergist with natural pyrethrins. The degree of potentiation of insecticidal activity is related to the ratio of components in the mixture; as the proportion of piperonyl butoxide increases, the amount of natural pyrethrins required to evoke the same level of kill decreases. The insecticidal activity of other pyrethroids, particularly of knockdown agents, can also be enhanced by the addition of piperonyl butoxide. The enhancement of activity of synthetic pyrethroids is normally less dramatic. Piperonyl butoxide inhibits the microsomal enzyme system of some arthropods and is effective against some mites. In addition to having low mammalian toxicity and a long record of safety, it rapidly degrades in the environment.

Various products from natural sources, as well as synthetic compounds, have been used as insect repellents. Such compounds include cinerins, pyrethrins and jasmolins, citronella, indalone, garlic oil, MGK-264, butoxypolypropylene-glycol, DEET, and DMP (dimethylphthalate). The use of repellents is advantageous as legislative and regulatory authorities become more restrictive toward the use of conventional pesticides. They are used mainly to protect horses against blood-sucking arthropods, particularly midges (*Culicoides*).

Insecticides may be used to provide environmental control of some insects by application to premises. The insect pheromone (Z)-9-tricosene is incorporated into some products to attract insects to the site of application.

In some embodiments, an insecticidal compound, including an ectoparasiticide used in the presently disclosed subject matter, can be applied topically to the skin, where the active ingredient is absorbed percutaneously and taken up into the circulation. Such insecticidal compounds can be provided in the form of an aqueous emulsion or suspension, i.e. a liquid. Such a form is compatible with use in an apparatus as disclosed herein, where the insecticidal compound is absorbed into or impregnated in the material of the apparatus.

The insecticidal apparatus disclosed herein, and methods of using the same, provide distinct advantages for controlling or managing insect pests and parasites. By way of example and not limitation, the apparatus disclosed herein does not require frequent recharges. Instead, in some embodiments, the apparatus can be installed and removed easily, with replacement required only after an impregnated insecticidal compound wears off. In some embodiments, an apparatus can last 6 to 12 weeks as compared to 1 to 2 weeks for currently existing methods of delivering ectoparasiticides and insecticidal agents.

An apparatus as disclosed herein can be placed strategically where animals will come into contact with the apparatus, thereby reducing the need to handle the animals to treat for ectoparasites. Existing approaches can require frequent administration of compounds to the livestock, which requires that the livestock be handled each time.

Currently, existing methods of delivering ectoparasiticides present the risk of contaminating feedstuffs. Since the disclosed apparatus is impregnated with an insecticidal compound there is little risk of feedstuff contamination.

The disclosed apparatus is durable and resist damage when used around animals, including large livestock animals. The design of the disclosed apparatus is devoid of complex mechanical structures which thereby minimizes mechanical failures. Further, the material from which the apparatus is made, e.g. PVC, is durable and weather resistant. Even in the event of damage to the apparatus, they are designed to be readily replaced at a relatively low cost.

Given their low cost and simplicity in design, the disclosed apparatus can be placed in a plurality of locations to thereby maximize exposure to the intended subject, e.g. animal or human. For example, unlike existing devices that are large, complex and/or expensive, the disclosed apparatus can be placed in a plurality of locations such as on rubs, at the entry to feeders or troughs (e.g. hay feeders, creep feeders, self-feeders, water sources, etc.), and in housing and handling facilities to thereby increase the exposure of livestock animals, for example, to the apparatus.

In livestock applications the need for frequent re-treatment and cost of ectoparasiticides is a significant factor is the use of ectoparasiticides. Costs can include the purchase price of the ectoparasiticide as well as any carrying agent. The disclosed apparatus can decrease the cost of using ectoparasiticides given its durable and flexible utility and cost-effective design.

In some embodiments, the insecticidal apparatus can be used for controlling insects and/or pests within a premise, such as in barns and/or stables, or a yard, home or building.

In some embodiments, the insecticidal apparatus can be used for extermination and control of pests. The size of the insecticidal apparatus, ingredient or type of ectoparasiticide, and concentration thereof can be selected based on the type of pest or pests to be controlled.

In some embodiments, the disclosed insecticidal apparatus can be used for bed bug control. By way of example and not limitation, the disclosed insecticidal apparatus can be placed under mattresses, in or around furniture, and in or near luggage to control the spread of bed bugs and infestations thereof.

In some embodiments, the disclosed insecticidal apparatus can be used for pest control outdoors. In some embodiments, a disclosed insecticidal apparatus can be attached or affixed to a clothing object worn on a person so as to position the apparatus in close proximity to the person. For example, the disclosed insecticidal apparatus can be hung from backpacks, used in boats and deer stands. The disclosed insecticidal apparatus can be placed on tables and on decks and docks. The disclosed insecticidal apparatus can control various nuisance pests such as house flies and biting pests such as mosquitoes, gnats, biting flies, house flies, and no-see-ums. The disclosed insecticidal apparatus can be used to control ticks, especially deer ticks. The disclosed insecticidal apparatus can be used for any outdoor activity, e.g. golf, fishing, hunting, hiking, camping, and can be placed on a person or article, e.g. hat, clothing, tent, golf bag. Unlike clip-on pest control devices currently available, in some embodiments the disclosed insecticidal apparatus do not require a refill. That is, the disclosed insecticidal apparatus have an active ingredient that is impregnated or imbedded in the carrier material, whereas existing clip-on devices comprise outer shell and internal compartment for holding an active ingredient. Furthermore, unlike table top candles or foggers, the disclosed insecticidal apparatus do not emit harmful fumes.

The disclosed insecticidal apparatus, can, in some embodiments, be placed in and/or around entryways to restaurants, grocery stores, and other businesses to control pests while minimizing contamination risks such as presented by foggers and sprayers.

In some embodiments, the disclosed insecticidal apparatus can be placed on fruit trees and vegetable plants for controlling pests without direct contamination of the fruit or vegetable.

In some embodiments, the disclosed insecticidal apparatus can be placed inside the cabin of an automobile, plane or equipment.

In some embodiments, the disclosed insecticidal apparatus can be placed inside or outside of tents for pest control.

In some embodiments, the disclosed insecticidal apparatus can be placed inside pet houses and/or kennels to control fleas and other pests.

In some embodiments, the disclosed insecticidal apparatus can be placed under houses and buildings to prevent damage caused by wood destroying insects such as borers and termites. In some embodiments, the disclosed insecticidal apparatus can be placed under homes and/or buildings offering a safer longer lasting pest control than powders or sprays where particles could directly contaminate the air and/or object they were applied to.

In some embodiments, the disclosed insecticidal apparatus can be placed inside homes to prevent pests such as roaches, ants and other house hold pests.

In some embodiments, the disclosed insecticidal apparatus can be placed in closets in place of moth balls to prevent clothes damaging pests, e.g. moths. In some embodiments, the disclosed insecticidal apparatus can be hung on hangers in closets.

In some embodiments, the disclosed insecticidal apparatus can be placed on lumber stacks to prevent wood destroying insects.

In some embodiments, the disclosed insecticidal apparatus can be used by soldiers on uniforms or gear.

In some embodiments, the disclosed insecticidal apparatus sizes can vary based on the desired or intended application. By way of example and not limitation, the disclosed insecticidal apparatus can be less than an inch in length with a width up to several inches or feet for broader based application. The active ingredient(s) of an the disclosed insecticidal apparatus can vary based on the application as well. The size of an the disclosed insecticidal apparatus and type and strength of the active ingredient can coincide with the desired application and intended use, e.g. pest control. For example, large strips several feet in length and/or width can be placed inside a building or outside for large events. Small strips less than an inch can be placed on a person.

Unlike foggers and/or candles, the disclosed insecticidal apparatus can be used indoors with less likelihood of contamination. In some embodiments, strips can be combined with mechanical objects, such as a fan, to reflect the active ingredient/insecticide. In some embodiments, the disclosed insecticidal apparatus can use color agent that can fade over time as the impregnated ingredient dissipates.

Methods of controlling and/or treating insect pests, ectoparasites, and the like are also disclosed herein. In some embodiments a method of controlling insect pests can comprise providing an apparatus for administering an insecticidal compound to an animal, wherein the apparatus can comprise a material for absorbing an insecticidal compound and an insecticidal compound, and placing the apparatus in a location where insect pest control is desired. In some aspects, an apparatus can be placed in or affixed to a location where it will come into contact with the subject to be treated. For example, affixing an insecticidal apparatus to a feeder can provide for the administration of an insecticidal compound to a livestock animal using the feeder, whereby insect pests and/or ectoparasites can be controlled on and around the animal. Alternatively, placing an insecticidal apparatus in a location where people congregate, e.g. an outdoor patio, can provide for the control of insect pests in the vicinity of the apparatus.

Such methods can further comprise administering an insecticidal compound to an absorbent material of an apparatus as disclosed herein. A method of controlling insect pests and/or ectoparasites can further comprise recharging or refilling an apparatus with an insecticidal compound.

The present subject matter can be embodied in other forms without departure from the spirit and essential characteristics thereof. The embodiments described therefore are to be considered in all respects as illustrative and not restrictive. Although the present subject matter has been described in terms of certain preferred embodiments, other embodiments that are apparent to those of ordinary skill in the art are also within the scope of the present subject matter.

What is claimed is:

1. An insect pest control system, comprising:
   a feeder configured to hold animal feedstuff and comprising an opening through which an animal can access the feedstuff, wherein the feeder comprises:
   (a) a cylindrical shaped pan having a bottom and sides forming a generally cylindrical outer periphery and recessed inner receptacle for holding feed;
   (b) a cylindrical shaped hood comprising a substantially cylindrical member affixed to and extending vertically from the pan;
   (c) an opening in the hood of a size sufficient to permit livestock to have access therethrough to the inner receptacle of the pan; and
   (d) a disc-shaped flange extending perpendicular from the cylindrical outer periphery of the sides of the pan and near the bottom of the pan, wherein a diameter of the disc-shaped flange is greater than the diameter of the cylindrical outer periphery of the pan, wherein the disc-shaped flange that extends from the cylindrical outer periphery of the sides of the pan provides a surface against which a base structure that can slidingly engage the outer periphery of the pan can abut, wherein the disc-shaped flange, by providing a surface against which a base structure can abut, can provide for the stabilization of the feeder, the disc-shaped flange is configured to rest on a ground surface when the feeder is in use as a livestock feeder, wherein the entire feeder is a single molded piece, wherein the bottom of the pan and disc-shaped flange together form a lower surface of the feeder, wherein the lower surface of the feeder forms a continuous planar surface configured to rest on a ground surface when the feeder is in use as a livestock feeder;

an apparatus for administering an insecticidal compound to an animal, the apparatus for administering the insecticidal compound comprising:

a material for absorbing an insecticidal compound;

an insecticidal compound, wherein the insecticidal compound is absorbed into at least a portion of the material; and an attachment element, wherein the insecticidal compound is capable of being administered to an animal that comes into contact with the apparatus; and an attachment element configured to attach the apparatus to the feeder at a location proximate to the opening through which an animal can access the feedstuff.

2. The system of claim 1, wherein the insecticidal compound is administered to the animal for up to about 6 to about 12 weeks.

3. The system of claim 1, wherein the apparatus for administering an insecticidal compound to an animal further comprises a color agent that fades as the insecticide compound dissipates from the material.

* * * * *